United States Patent
Piferi (10) Patent No.: US 9,031,636 B2
(45) Date of Patent: May 12, 2015

(54) MRI-COMPATIBLE HEAD FIXATION APPARATUS

(71) Applicant: MRI Interventions, Inc., Memphis, TN (US)

(72) Inventor: Peter Piferi, Orange, CA (US)

(73) Assignee: MRI Interventions, Inc., Memphis, TN (US)

(*) Notice: Subject to any disclaimer, the term of this patent is extended or adjusted under 35 U.S.C. 154(b) by 142 days.

(21) Appl. No.: 13/781,117

(22) Filed: Feb. 28, 2013

(65) Prior Publication Data

US 2014/0024925 A1 Jan. 23, 2014

Related U.S. Application Data

(60) Provisional application No. 61/673,491, filed on Jul. 19, 2012.

(51) Int. Cl.
*A61B 5/055* (2006.01)
*A61B 5/00* (2006.01)
*A61B 5/05* (2006.01)

(52) U.S. Cl.
CPC ............ *A61B 5/0555* (2013.01); *A61B 5/6814* (2013.01)

(58) Field of Classification Search
CPC ......... A61B 5/0555; A61B 6/04; A61B 19/00
USPC .................................................. 600/415, 417
See application file for complete search history.

(56) References Cited

U.S. PATENT DOCUMENTS

| 5,276,927 A * | 1/1994 | Day .................................. 5/622 |
| 8,099,150 B2 * | 1/2012 | Piferi et al. .................. 600/422 |
| 8,844,536 B1 * | 9/2014 | Schuele ........................ 128/845 |
| 2010/0185198 A1 | 7/2010 | Piferi et al. |

FOREIGN PATENT DOCUMENTS

| JP | 11-004837 A | 1/1999 |
| JP | 2000-175937 A | 6/2000 |
| JP | 2002-233523 A | 8/2002 |
| WO | WO 0047155 A1 | 8/2000 |

OTHER PUBLICATIONS

Notification of Transmittal of the International Search Report and The Written Opinion of the International Searching Authority, or the Declaration; International Search Report; and Written Opinion of the International Searching Authority; Date of Mailing Sep. 26, 2013; 10 pages.
Notification of Transmittal of International Preliminary Report on Patentability, PCT/US2013/045377, Date of Mailing Nov. 7, 2014; 5 pages.

* cited by examiner

*Primary Examiner* — Long V Le
*Assistant Examiner* — Katherine McDonald
(74) *Attorney, Agent, or Firm* — Myers Bigel Sibley & Sajovec (57) ABSTRACT

An MRI-compatible base is configured to support an MRI-compatible head support frame. The base is configured to be secured to a gantry associated with an MRI scanner, and to extend across a width of the gantry. The base allows the head support frame to be moved to any of a plurality of locations across the width of the gantry, and allows the head support frame to rotate about two orthogonal axes so as to be positioned at any of a plurality of angles relative to the gantry.

12 Claims, 12 Drawing Sheets

MRI-COMPATIBLE HEAD FIXATION APPARATUS

RELATED APPLICATION

This application claims the benefit of and priority to U.S. Provisional Patent Application No. 61/673,491 filed Jul. 19, 2012, the disclosure of which is incorporated herein by reference as if set forth in its entirety.

FIELD OF THE INVENTION

The present invention relates generally to medical systems and apparatus and, more particularly, to MRI-interventional systems and apparatus.

BACKGROUND

During MRI-Guided surgeries, it can be desired to drill through bone such as a skull to define a surgical path for passing medical interventional devices.

SUMMARY

According to some embodiments of the present invention, an apparatus for securing various types of head support frames within a bore of an MRI scanner includes an elongated base formed entirely of MRI compatible material. The base is configured to be secured to a gantry associated with an MRI scanner and to extend across a width of the gantry. The base is configured to removably receive an MRI compatible head support frame for adjustably immobilizing the head of a patient during a medical procedure, and to allow the head support frame to be moved to any of a plurality of locations across the width of the gantry. The base allows the head support frame to rotate about two orthogonal axes so as to be positioned at any of a plurality of angles relative to the gantry, and allows the head support frame to slide along the base to any of a plurality of positions relative to the width of the gantry.

In some embodiments, the base includes a pair of support members and an elongated member that extends therebetween. The elongated member is movably coupled to the support members such that the elongated member can be rotated axially. A head support frame is slidably secured to the elongated member and can be positioned at any of a plurality of locations between the support members.

In some embodiments, the elongated member has a substantially rectangular cross section.

In some embodiments, each support member includes a lower surface that is oriented at an angle relative to a longitudinal direction of the elongated member.

In some embodiments, each support member includes a lower surface and a gripping element that extends outwardly from the lower surface. The gripping element may extend outwardly from the lower surface at an acute angle (e.g., an angle of less than 90°) relative to the lower surface.

According to some embodiments of the present invention, a head fixation assembly includes an elongated base and a head support frame movably attached to the base. The base is formed entirely of MRI compatible material and is configured to removably receive the head support frame for adjustably immobilizing the head of a patient during a medical procedure. The base is configured to be secured to a gantry associated with an MRI scanner and to extend across a width of the gantry. In some embodiments, the base is secured to the gantry or to another device that is secured to the gantry.

The head support frame includes a pair of head engagement arms that extend outwardly in adjacent, spaced-apart relationship. Each head engagement arm has a free end and at least one head fixation member configured to engage a patient's head within the head support frame and restrain the patient's head from movement. In addition, the head support frame is rotatable about two orthogonal axes so as to be positioned at any of a plurality of angles relative to the gantry.

In some embodiments, one of the head engagement arms has an arcuate carrier that is pivotably secured thereto and that supports a pair of spaced-apart head fixation members configured to engage a patient's head.

The head support frame is slidable along the base so as to be positioned at any of a plurality of locations across the width of the gantry. In some embodiments of the present invention, the base includes a pair of support members and an elongated member that extends between and is movably coupled to the support members. The elongated member has opposite first and second end portions, and each of the first and second end portions includes a free end portion that is received within a respective bore in a respective one of the supports such that the elongated member can be rotated axially. The head support frame is slidably secured to the elongated member and can be positioned at any of a plurality of locations between the support members.

In some embodiments of the present invention, a first connector surrounds a free end portion of the elongated member and includes a plurality of engagement teeth. A support that receives the free end portion includes a second connector that has a plurality of engagement teeth configured to mateably engage with the engagement teeth of the first connector to prevent axial rotation of the elongated member.

In some embodiments of the present invention, the elongated member comprises a connector housing that is slidably secured thereto. A shaft having a free distal end extends outwardly from the connector housing. A first connector surrounds the shaft and includes a plurality of engagement teeth. The head support frame includes a bore extending through one of the head engagement arms that is configured to receive the shaft. A second connector surrounds the bore and has a plurality of engagement teeth configured to mateably engage with the engagement teeth of the first connector to prevent axial rotation of the shaft.

In some embodiments of the present invention, the head engagement arms have a generally L-shaped configuration and are movable relative to each other such that a distance between the free ends of the head engagement arms is adjustable. In some embodiments of the present invention, the head engagement arms are slidably engaged with each other.

In some embodiments of the present invention, a section of a first head engagement arm having rack teeth is telescopically received inside an elongated opening in a section of the second head engagement arm. A pawl is operably mounted in the elongated opening and is configured to engage the rack teeth and to hold the head engagement arms against movement in a direction to cause separation of the head engagement arms.

In some embodiments of the present invention, a flexible RF coil is attached to each head engagement arm of the head support assembly.

Head fixation assemblies according to embodiments of the present invention may be particularly suitable for placing neuro-modulation leads, such as Deep Brain Stimulation ("DBS") leads, implantable parasympathetic or sympathetic nerve chain leads and/or CNS stimulation leads, as well as other devices within the brain. Embodiments of the present invention may be suitable for a number of MRI-guided drug delivery procedures, MRI-guided ablation procedures, etc.

Head fixation assemblies according to embodiments of the present invention can be advantageous over conventional systems because they can be easily adjustable for various patient head sizes and shapes, and can support large forces exerted in any direction without movement, thereby providing stability to the head of a patient during various interventional procedures. In addition, head support assemblies according to embodiments of the present invention do not allow a patient's head to move in any direction, including pivotal movement. Moreover, head fixation assemblies according to embodiments of the present invention do not interfere with other components or a physician's access to the patient. Head fixation assemblies, according to embodiments of the present invention can be sterilized within an autoclave, and can be wiped down with disinfectant and cleaners. Head fixation assemblies, according to embodiments of the present invention can be installed and used many times without degradation, or may be single-use and disposable.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

FIGS. 7A-7B are end perspective views illustrating a head fixation assembly according to other embodiments of the present invention, with the head fixation assembly shown supporting a phantom patient head. FIGS. 7A-7B illustrate left and right movement of the head support frame, as well as sliding movement of the head support frame along the base.

DETAILED DESCRIPTION

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "about", as used herein with respect to a value or number, means that the value or number can vary by +/−twenty percent (20%).

The term "MRI compatible" means that a device is safe for use in an MRI environment and/or can operate as intended in an MRI environment without generating MR signal artifacts, and, as such, if residing within the high-field strength region of the magnetic field, is typically made of a non-ferromagnetic MRI compatible material(s) suitable to reside and/or operate in a high magnetic field environment.

The term "gantry" refers to a patient support, for example, associated with an MRI scanner, and may include a patient table or other structure.

The term "head fixation member" refers to an elongate member with sufficient structural rigidity to secure and/or move the head of a patient and may take the form of a bolt, pin, screw, etc. Head fixation members according to various embodiments of the present invention may be threaded skull pins.

The term "head fixation assembly" refers to an assembly including at least a head support frame and a base for supporting the head support frame, as described in more detail below. Head fixation assemblies according to various embodiments of the present invention may further include a head coil apparatus and/or associated components, as further described in more detail below.

Head fixation assemblies according to embodiments of the present invention facilitate guiding and/or placing diagnostic or interventional devices and/or therapies to any desired internal region of the brain. For example, head fixation assemblies according to embodiments of the present invention facilitate the placement of implantable DBS leads for brain stimulation, typically deep brain stimulation, and facilitate delivering tools or therapies that stimulate a desired region of the sympathetic nerve chain. Embodiments of the present invention can be used with any MRI scanner system, including open and closed bore designs and any field strength, typically 1.0 T (Tesla)-10 T, such as about 1.5 T and 2.0 T.

Embodiments of the present invention have other uses inside or outside the brain including stem cell placement, gene therapy or drug delivery for treating physiological conditions. Some embodiments can be used to treat tumors. Some embodiments can be used for diagnosing or delivering any desired therapy such as, for example, RF stimulation or ablation, laser stimulation or ablation, cryogenic stimulation or ablation, etc.

Embodiments of the present invention will now be described in detail below with reference to the figures. Referring initially to FIGS. 1-4, a head fixation assembly 10 is illustrated and includes a base 20 and a head support frame 60 movably secured to the base 20. The base 20 and head support frame 60 are MRI compatible. The base 20 is designed to accept different types of head support frames 60 from various manufacturers. Embodiments of the present invention are not limited to the illustrated head support frame 60.

The illustrated base 20 includes spaced apart first and second supports 22a, 22b connected by an elongated member 24 secured therebetween. In some embodiments, the first and second supports 22a, 22b are configured to be secured to a gantry (e.g., "G", FIGS. 9-11) associated with an MRI scanner. Each of the first and second supports 22a, 22b may include one or more passageways formed therethrough (e.g., 23, FIGS. 7A-7B) and through which one or more fasteners (e.g., set screws, bolts, or other locking mechanisms) can be inserted to secure the support to a selected location of a gantry. However, a variety of ways of securing the base 20 to a gantry G may be utilized.

In some embodiments of the present invention, the base 20 may not be attached directly to an MRI scanner gantry. Instead, the base 20 may be configured to be connected to or integrated with another device that could be received and secured to an MRI scanner or to a gantry associated with an MRI scanner. As such, embodiments of the present invention are not limited to the illustrated configuration of base 20 and supports 22a, 22b. The MRI compatible base 20 that is configured to receive a head support frame 60 and allow the head support frame to be moved along the base 20 relative to a gantry of an MRI scanner can have various configurations.

Figure 3:
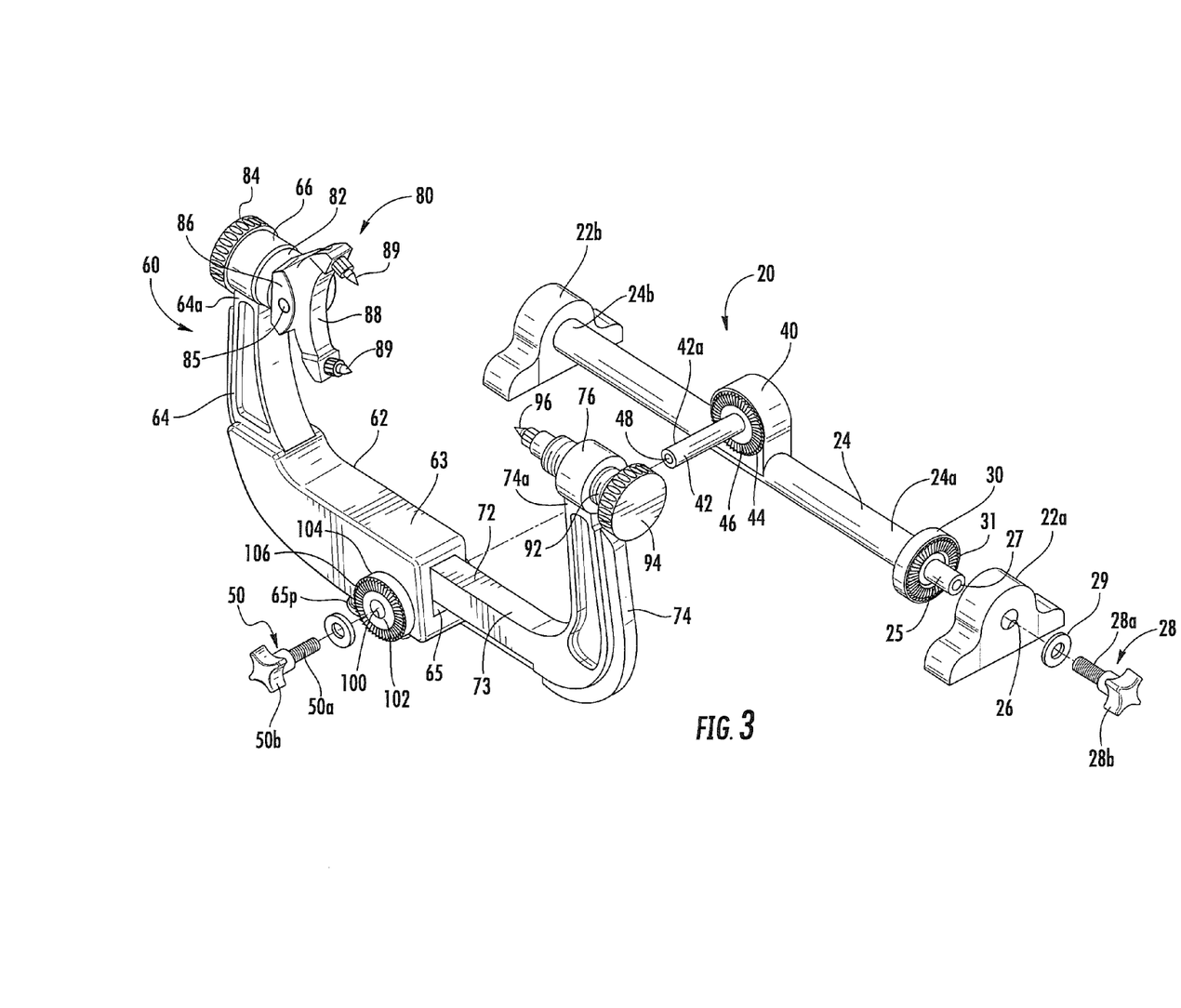
FIGS. 3 and 4 are front and rear exploded views, respectively, of the head fixation assembly of FIG. 1.
Figure 4:
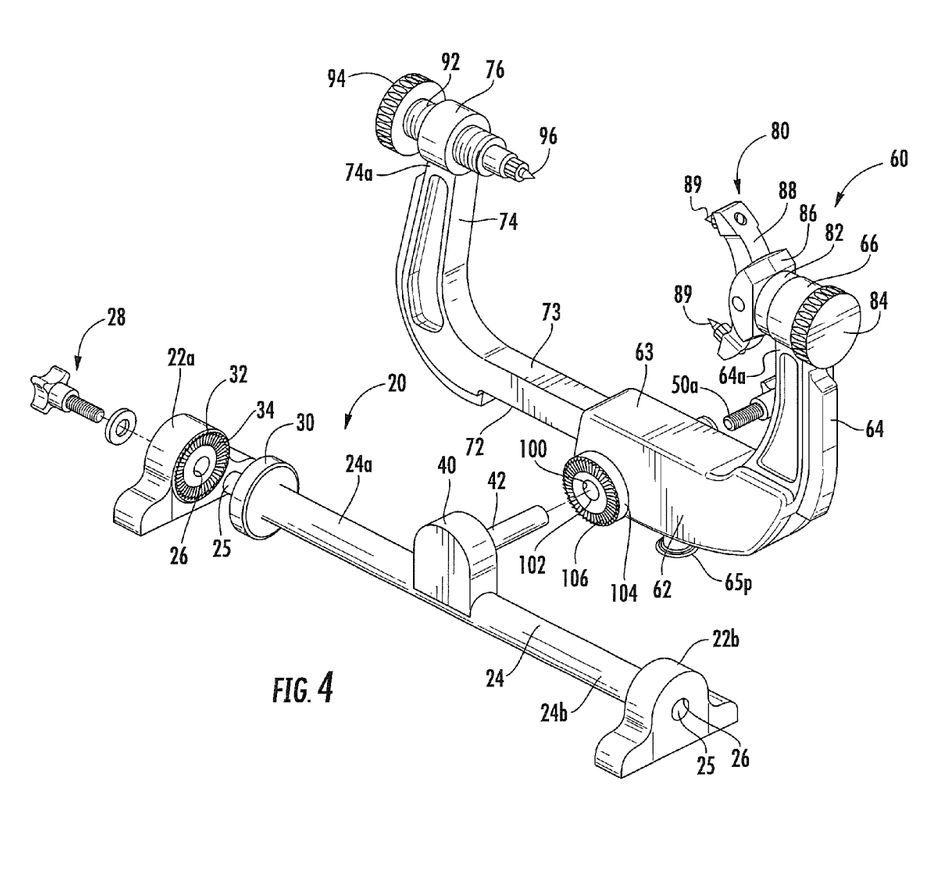

As shown in FIGS. 3 and 4, the elongated member 24 has opposite first and second end portions 24a, 24b. Each of the first and second end portions 24a, 24b includes a free end portion 25 that is received within a bore 26 in a respective one of the supports 22a, 22b. The bore 26 in each of the supports 22a, 22b can serve as a bearing and facilitate axial rotation of the elongated member 24. The free end portion 25 at the elongated member first end portion 24a includes a threaded axial bore 27, as illustrated in FIG. 3. The threaded bore 27 is configured to receive a threaded locking member 28, as will be described below.

The first end portion 24a of the elongated member 24 includes a connector 30 that surrounds the cylindrical free end portion 25 and that has a plurality of engagement teeth 31, as illustrated in FIG. 3. The support 22a that receives the free end portion 25 of the elongated member first end portion 24a includes a connector 32 that surrounds the bore 26 and that has a plurality of engagement teeth 34 that are configured to mateably engage with the engagement teeth 31 of connector 30, as illustrated in FIG. 4. The threaded locking member 28 includes a threaded portion 28a and a handle 28b. The handle 28b facilitates tightening and loosening of the locking member 28 by hand. A washer 29 is also provided in the illustrated embodiment, as would be understood by those skilled in the art of the present invention.

To rotate the elongated member 24 about its axis, the locking member 28 is loosened by rotating the handle 28b such that the teeth 31 of connector 30 can become disengaged from the teeth 34 of connector 32. The elongated member 24 can then be axially rotated, typically by any desired amount. To maintain the elongated member 24 in the desired rotated position, the locking member 28 is tightened to cause the teeth 31 of connector 30 to engage with the teeth 34 of connector 32 which, thereby, restrains the elongated member 24 from axial rotation.

Figure 7A:
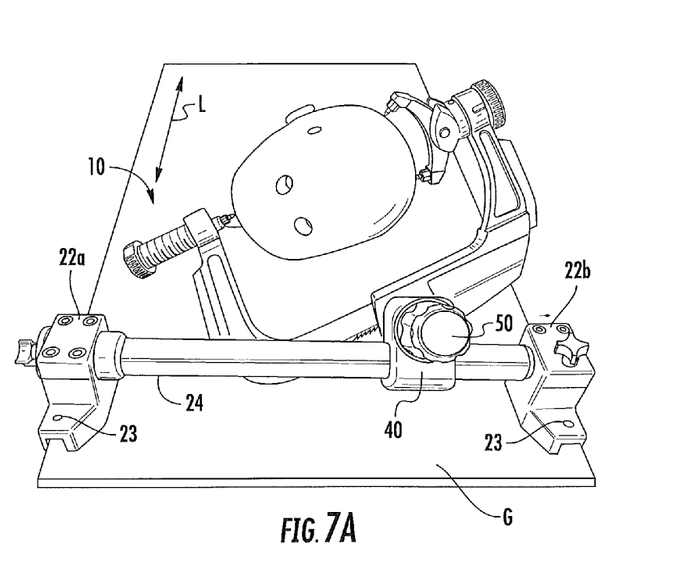
Figure 7B:
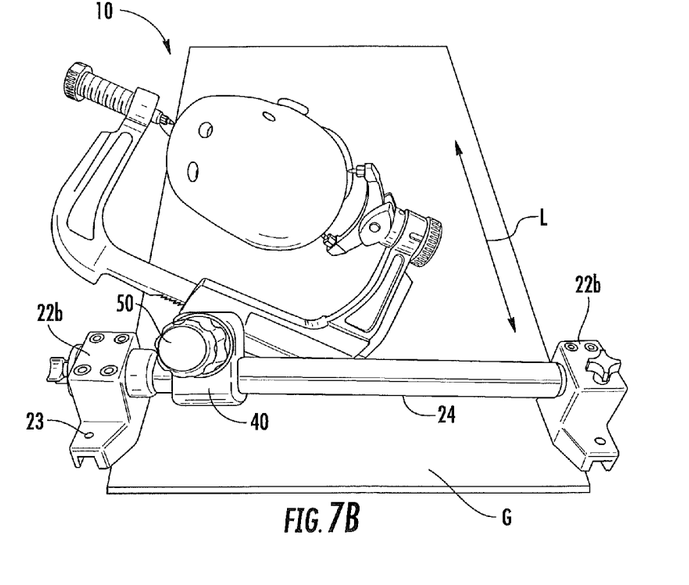

A connector housing 40 is slidably secured to the elongated member 24 of the base 20. As illustrated in FIGS. 7A-7B, the connector housing 40 allows the head support frame 60 to be positioned at any location between the supports 22a, 22b. Referring to FIGS. 3 and 4, a shaft 42 having a free distal end 42a extends outwardly from the connector housing 40. A connector 44 having a plurality of engagement teeth 46 surrounds the shaft 42, as illustrated in FIG. 3. The shaft 42 includes has a generally cylindrical configuration. The shaft 42 can include a threaded bore 48 that terminates at the distal free end, as illustrated in FIG. 3. The shaft 42 is configured to support the head support frame 60 and permit rotation of the head support frame 60 about an axis of the shaft 42. The threaded bore 48 can be configured to receive a threaded locking member 50, as will be described below.

Embodiments of the present invention are not limited to the illustrated base 20. Furthermore, it is anticipated that the base 20 can be customized to fit and be secured to any type of gantry or device attached to a gantry. That is, the base 20 may be a universal base usable with several different MRI scanners from different manufacturers, may be MRI scanner type specific, or may be MRI scanner manufacturer specific.

Figure 11:
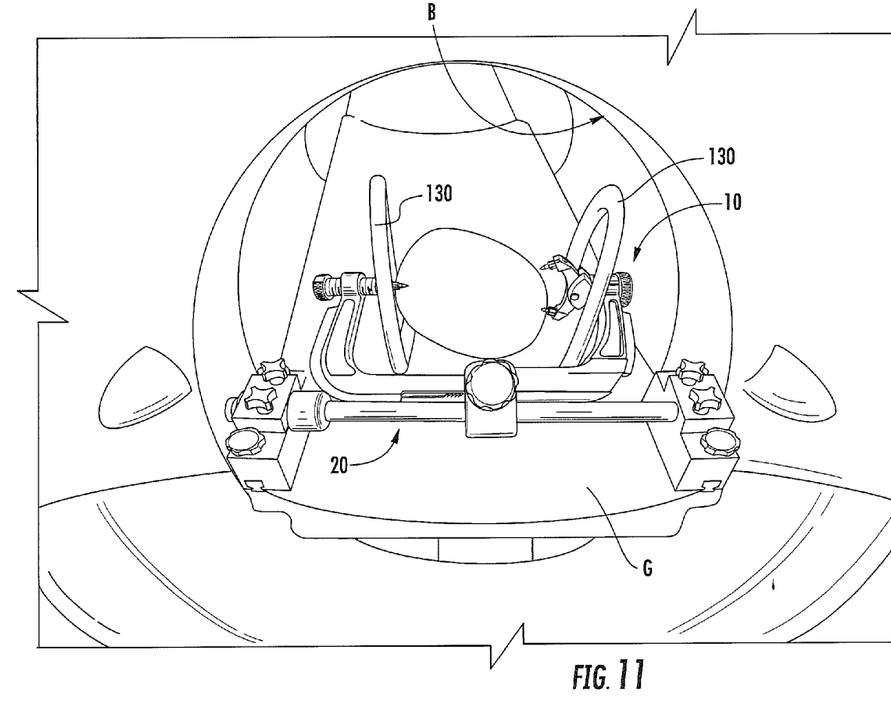
FIG. 11 illustrates a pair of flexible MRI coils that can cooperate with a head fixation assembly, according to some embodiments of the present invention.
Figure 12:
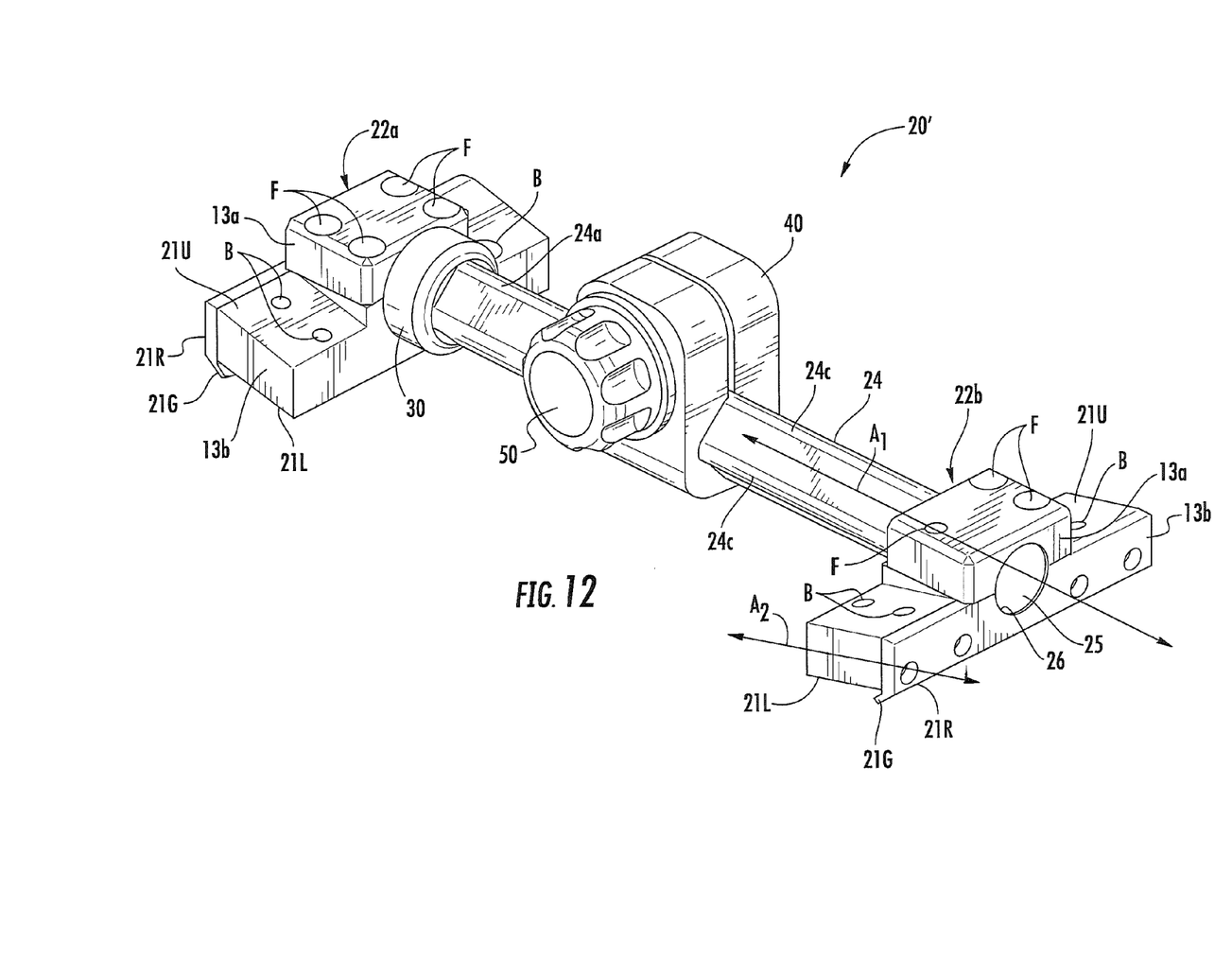
FIG. 12 is a perspective view of a base for supporting a head fixation frame, according to some embodiments of the present invention.

Referring to FIG. 12 a base 20' according to other embodiments of the present invention is illustrated. The illustrated base 20' of FIG. 12 is similar to the base 20 of FIGS. 1-4, 7A-7B, and 8-11 in configuration and function. The illustrated base 20' includes an elongated member 24 having opposite first and second end portions 24a, 24b. Each of the first and second end portions 24a, 24b includes a free end portion 25 that is received within a bore 26 in a respective one of the supports 22a, 22b. The bore 26 in each of the supports 22a, 22b serves as a bearing and facilitates axial rotation of the elongated member 24. The free end portion 25 at the elongated member first end portion 24a can include a threaded axial bore (not shown) that is similar to the threaded axial bore 27 of the base 20 illustrated in FIG. 3. The threaded bore is configured to receive a threaded locking member (not shown) as described above to allow the elongated member 24 to be rotated about it axis and to secure the elongated member 24 in a desired rotated position.

The first end portion 24a of the elongated member 24 includes a connector 30 that surrounds the free end portion (not shown) and that has a plurality of engagement teeth (not shown), as described above with respect to FIG. 3. The support 22a that receives the free end portion of the elongated member first end portion 24a also includes a connector (not shown) that surrounds the bore 26 and that has a plurality of engagement teeth (not shown) that are configured to mateably engage with the engagement teeth of connector 30, as described above with respect to FIG. 4.

The elongated member 24 has a substantially rectangular cross-sectional configuration with rounded or beveled edges 24c and flat surfaces 24d, as illustrated. However, embodiments of the present invention may utilize an elongated member 24 with other cross-sectional configurations. For example, the elongated member 24 may have a substantially triangular cross-sectional configuration, a pentagonal cross-sectional configuration, a hexagonal cross-sectional configuration, etc., and with or without rounded or beveled edges. In some embodiments, elongated member 24 may have a substantially circular cross-sectional configuration The supports 22a, 22b of the illustrated base 20' include an upper portion 13a and a lower portion 13b with a semi circular cavity or channel secured together via fasteners F, such as bolts or screws. The bore 26 in each of the supports 22a, 22b is formed when the channels of the upper and lower portions 13a, 13b meet when the upper and lower portions 13a, 13b are secured to each other. Each support lower portion 13b can be angled downwardly, as represented by arrow $A_2$, relative to the longitudinal axial direction of the elongated member 24, represented by arrow $A_1$. Each support lower portion 13b can have an upper surface 21U and a lower surface 21L. A plurality of bores B are formed through each support lower portion 13b and are configured to receive fasteners therethrough for securing the base 20' to an MRI scanner gantry or other device associated with the gantry.

As shown, each support lower portion 13b can include a gripping element 21G that extends downwardly from the lower surface 21L at a rear edge portion 21R thereof. The gripping element 21G is oriented at an angle relative to the lower surface 21L. The gripping element 21G and lower surface 21L are configured to engage a particular MRI gantry, or other device attached to an MRI gantry. The configuration of the gripping element 21G is such that an edge portion of a gantry or other device attached to the gantry can be gripped by the supports 22a, 22b. Typically, the base 20' slidably engages a gantry, or other device attached to the gantry, at an end portion of the gantry, or other device attached to the gantry, and is moved longitudinally along the gantry to a desired location.

The illustrated base 20' includes a connector housing 40 slidably secured to the elongated member 24 and that allows a head support frame secured thereto to be positioned at any location between the supports 22a, 22b, as described above with respect to base 20. A head support frame is secured to the base 20 by inserting a shaft extending from the head support frame into the connector housing 40. The shaft has a threaded axial bore and the locking member 50 is threadingly engaged with the threaded axial bore of the shaft, as described. The illustrated locking member 50 includes a threaded portion 50a and a handle 50b. The threaded portion 50a is threadingly engaged with the internally threaded bore 48 of the shaft, as described below with respect to FIGS. 1-4. The locking member 50, thus, serves two functions. The locking member 50 secures a head support frame to the base 20. In addition, by slightly loosening the locking member 50, the connector housing 40 can be slightly spread apart relative to the elongated member 24 and the connector housing 40 and head support frame secured thereto can be moved along the elongated member 24 of the base. Once moved to the desired location along the elongated member 24, the locking member 50 can be fully tightened and the connector housing 40 and head support frame secured thereto are locked into place.

Referring back to FIGS. 1-4, the illustrated head support frame 60 is an exemplary head support frame that can be used in conjunction with the base 20, 20' and includes first and second head engagement arms 62, 72, each of which has a generally "L-shaped" configuration to define a frame with a generally elongated "U-shape". The first head engagement arm 62 includes a first section 63 and a second section 64, and the second head engagement arm 72 includes a first section 73 and a second section 74. In the illustrated embodiment, the first and second sections 63, 64 of the first head engagement arm 62 are oriented so as to define an angle of about ninety degrees (90°), and the first and second sections 73, 74 of the second head engagement arm 72 are oriented so as to define an angle of somewhat less than about ninety degrees (90°). However, the first and second head engagement arms 62, 72 may have configurations with various angles (e.g., angles greater than 90° and angles less than 90°). Embodiments of the present invention are not limited to the illustrated configurations of the first and second head engagement arms 62, 72.

Figure 5:
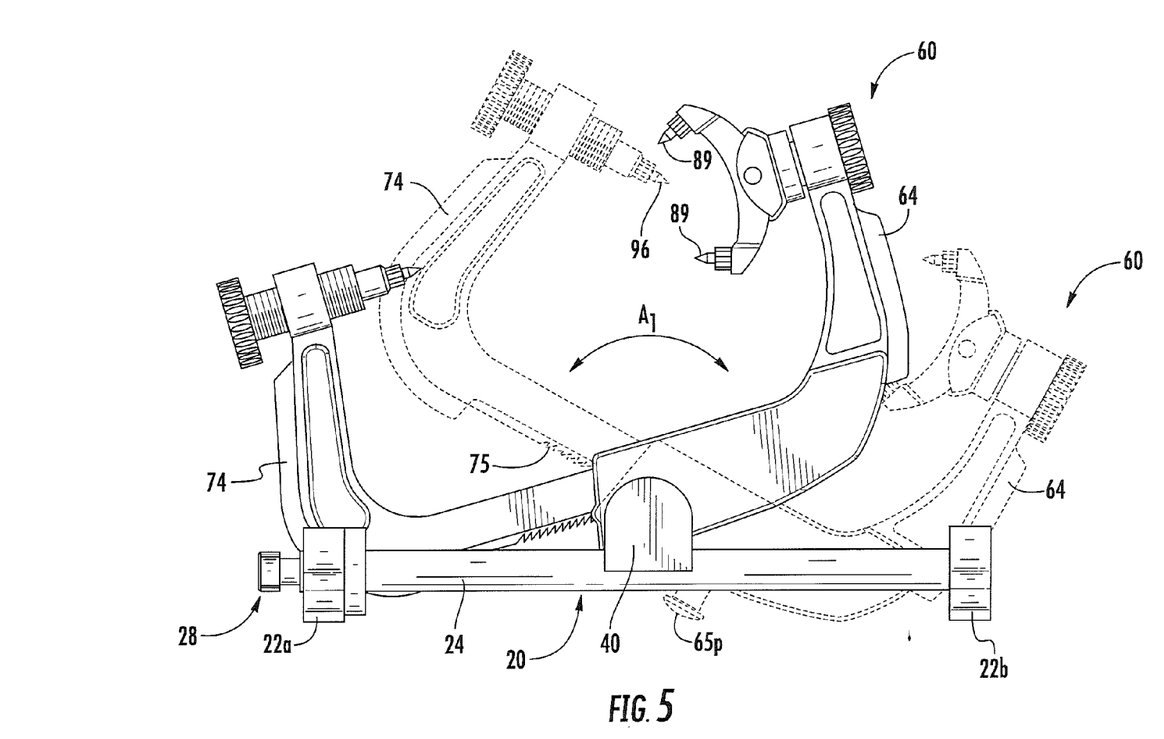
FIG. 5 is an end view of the head fixation assembly of FIG. 1 illustrating left and right movement of the head support frame.

The first section 73 of the second head engagement arm 72 is slideably and telescopically received inside an elongated opening 65 in the first section 63 of the first head engagement arm 62. The first section 73 of the second head engagement arm 72 has rack teeth 75 along a portion thereof (FIG. 5). A pawl 65p is slideably mounted in opening 65 in the first section 63 of the first arm 62. The pawl 65p includes teeth (not shown) that can engage the rack teeth 75 to hold the first and second head engagement arms 62, 72 against movement in a direction to cause separation of the first and second head engagement arms 62, 72. A spring may be attached to the first section 63 of the first head engagement arm 62 to urge the pawl 66 to a latched position, as would be understood by those skilled in the art of the present invention. The pawl 65p can be withdrawn against the pressure of the spring to release the pawl teeth from the rack teeth 75, thereby permitting movement of the first and second head engagement arms 62, 72 away from each other. The rack teeth 75 are constructed to restrain movement of the first and second head engagement arms 62, 72 away from each other but to permit movement toward each other, as would be understood by those skilled in the art of the present invention.

The first head engagement arm second section 64 includes an internally threaded boss 66 at a free end 64*a* thereof. A head engagement assembly 80 is threadingly engaged with the internally threaded boss 66 on the first head engagement arm 62. The head engagement assembly 80 includes a threaded carrier 82 that is threadingly engaged with the internally threaded boss 66. At one end, the threaded carrier 82 includes a handle 84 configured to be gripped by a user for rotation of the threaded carrier 82. At an opposite end, the threaded carrier 82 includes a pair of spaced-apart brackets 86. An arcuate carrier 88 that supports a pair of head fixation members (e.g., skull engagement pins) 89 is pivotably secured to the threaded carrier 82 between the bracket 86 via a pin or other connector 85. The illustrated head fixation members 89 are pins that have a conical shape that is configured to engage the skull of a patient's head and make sufficient contact with the skull to maintain the patient's head in a desired orientation. Because of the arcuate configuration of the carrier 88, the head fixation members 89 are oriented at a converging angle, as illustrated. The head fixation members 89 may be formed from non-ferromagnetic various materials (e.g., titanium, etc.) and may be disposable. The arcuate carrier 82 is configured to pivot to facilitate alignment of the head fixation members 89 with a patient's head.

The second head engagement arm second section 74 includes an internally threaded boss 76 at a free end 74*a* thereof. A threaded carrier 92 is threadingly engaged with the internally threaded boss 76. At one end, the threaded carrier 92 includes a handle 94 configured to be gripped by a user for rotation of the threaded carrier 92. At an opposite end, the threaded carrier 92 includes a head fixation member (e.g., a skull engagement pin) 96 similar to head fixation members 89. The head fixation member 96 can be a pin that has a conical shape that is configured to engage the skull of a patient's head and make sufficient contact with the skull to maintain the patient's head in a desired orientation. The head fixation member 96 may be formed from various non-ferromagnetic materials (e.g., titanium, etc.) and may be disposable.

The threaded bosses 66, 76 may each have an axial direction that is orthogonal to a longitudinal direction L of a gantry (FIGS. 7A-7B). Alternatively, one or both of the threaded bosses 66, 76 may have an axial direction that is non-orthogonal to the longitudinal direction L.

The first head engagement arm first section 63 includes a bore 100 extending therethrough and terminating at openings 102. A respective connector 104 surrounds each of the openings 102, and each connector 104 includes a plurality of engagement teeth 106, as illustrated in FIGS. 3 and 4. The head support frame 60 is secured to the base 20 by inserting the shaft 42 through the bore 100 such that the teeth 46 of connector 44 engage with the teeth 106 (FIG. 4) of connector 104, and then threadingly engaging the locking member 50 into the axial bore 48 of the shaft 42. The illustrated locking member 50 includes a threaded portion 50*a* and a handle 50*b*. The threaded portion 50*a* is threadingly engaged with the internally threaded bore 48 of the shaft.

Figure 6:
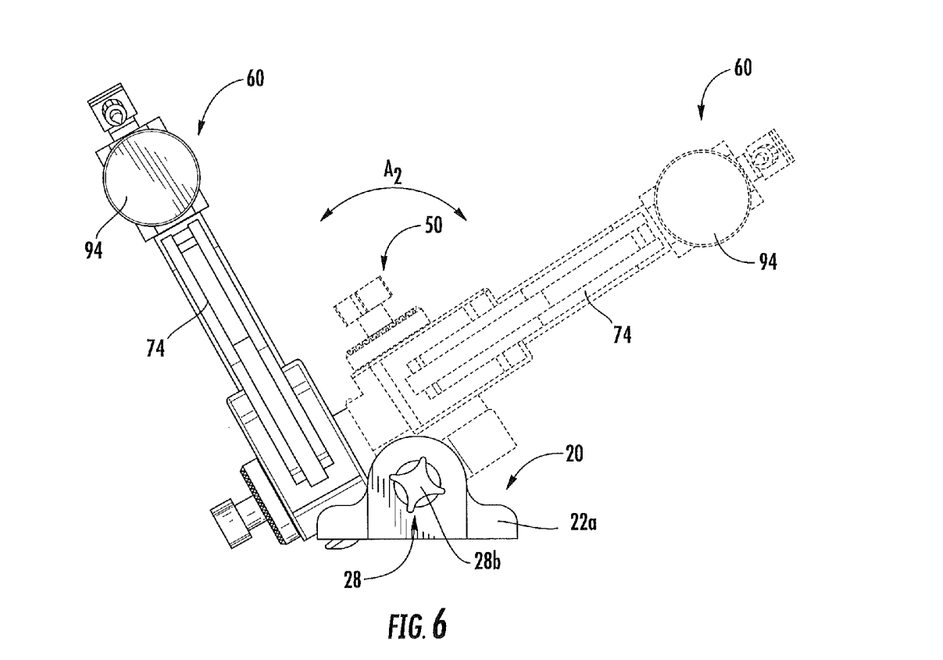
FIG. 6 is a side view of the head fixation assembly of FIG. 1 illustrating forward to back movement of the head support frame.

Left to right movement of the head support frame 60 is illustrated in FIG. 5, and indicated by arrow $A_1$. This movement is accomplished by loosening locking member 50 and rotating the head support frame 60 about shaft 42. FIGS. 7A-7B illustrate the head support frame 60 supporting a phantom of a patient's head and illustrating left and right movement of the head. Forward to back movement of the head support frame 60 is illustrated in FIG. 6, and indicated by arrow $A_2$. This movement is accomplished by loosening locking member 28 and rotating the elongated member 24 of the base 20 about its axis. As such, the head support frame 60 is rotatable about two orthogonal axes so as to be positioned at any of a plurality of angles/orientations relative to a gantry G.

Figure 1:
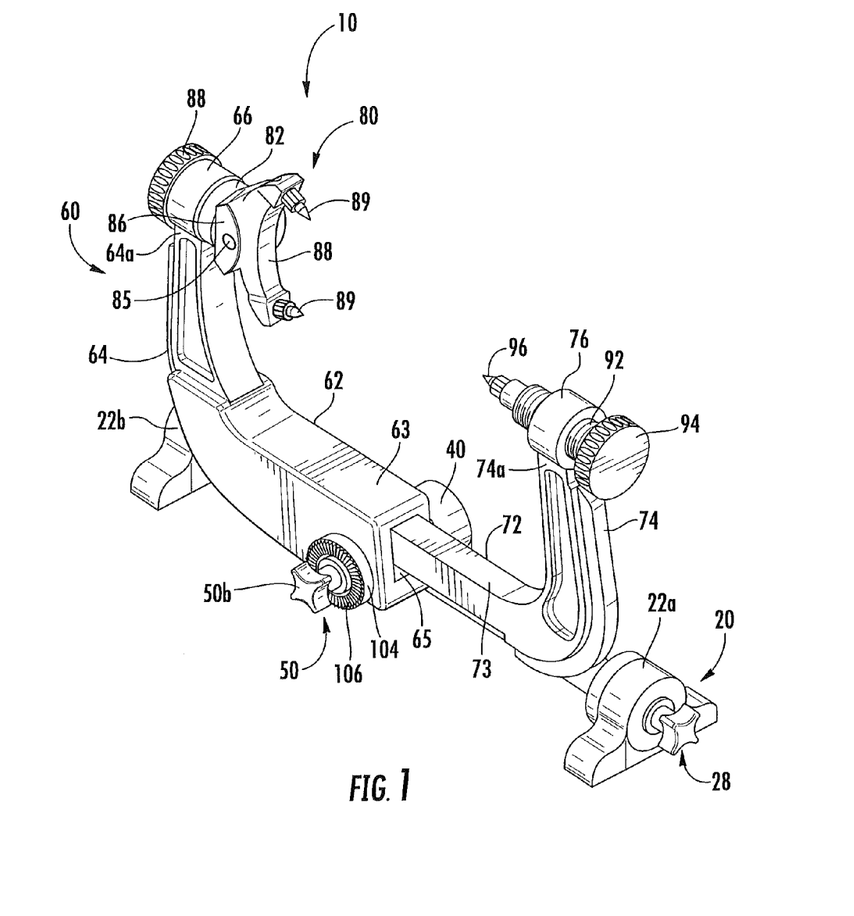
FIG. 1 is a front perspective view of a head fixation assembly, according to some embodiments of the present invention.
Figure 2:
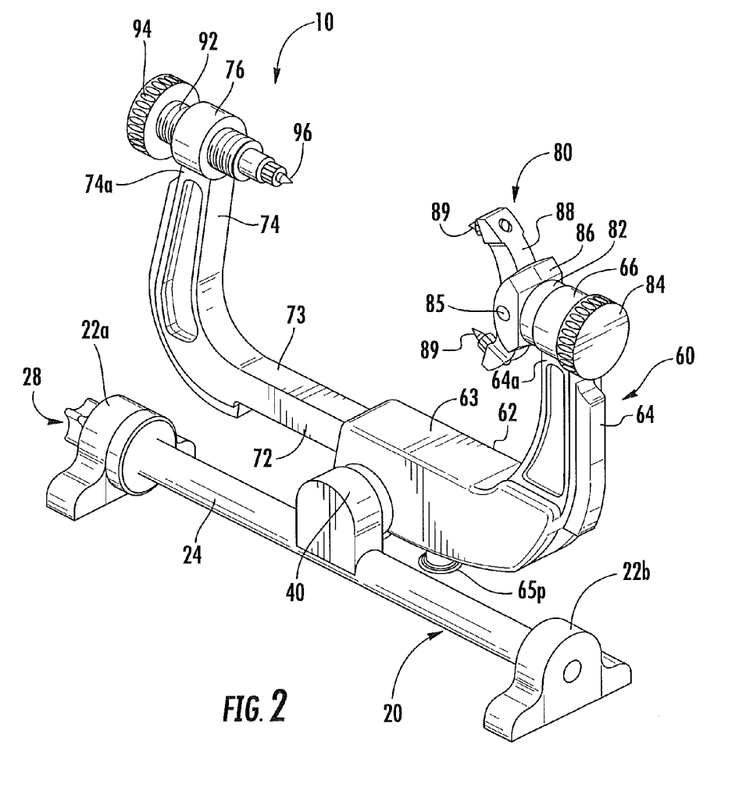
FIG. 2 is a rear perspective view of the head fixation assembly of FIG. 1.
Figure 8:
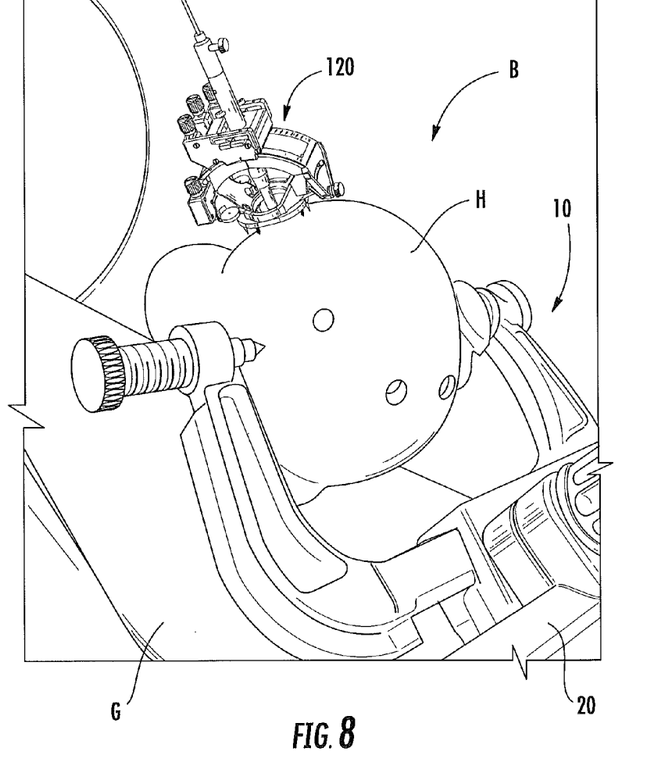
FIG. 8 is a top perspective view that illustrates the head fixation assembly of FIGS. 7A-7B supporting a phantom of a patient's head and positioned on a scanner bed/gantry within a bore of an MRI magnet, and also illustrating a targeting frame attached to a phantom patient head.

FIG. 8 illustrates the head fixation assembly 10 of FIG. 1 supporting a patient head H and positioned within a bore B of an MRI scanner magnet. The base 20 of the head fixation assembly 10 is secured to a gantry G associated with the magnet bore B of an MRI scanner. A targeting frame 120 is attached to the patient's head H, as illustrated.

Figure 9:
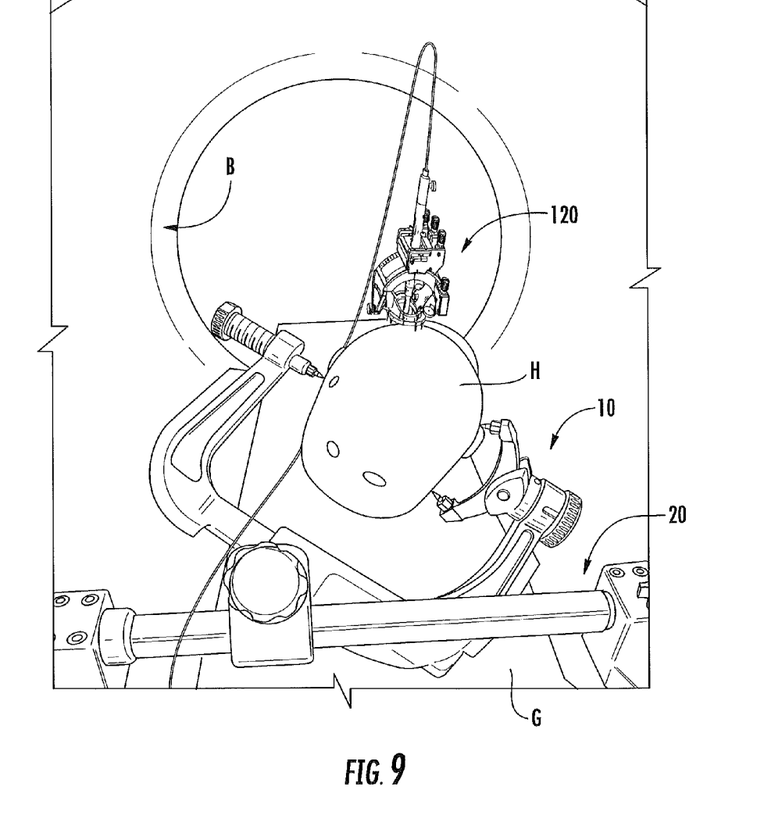
FIG. 9 illustrates the head fixation assembly of FIG. 8 with the targeting frame and phantom patient head in a first orientation relative to the bore of the MRI magnet.
Figure 10:
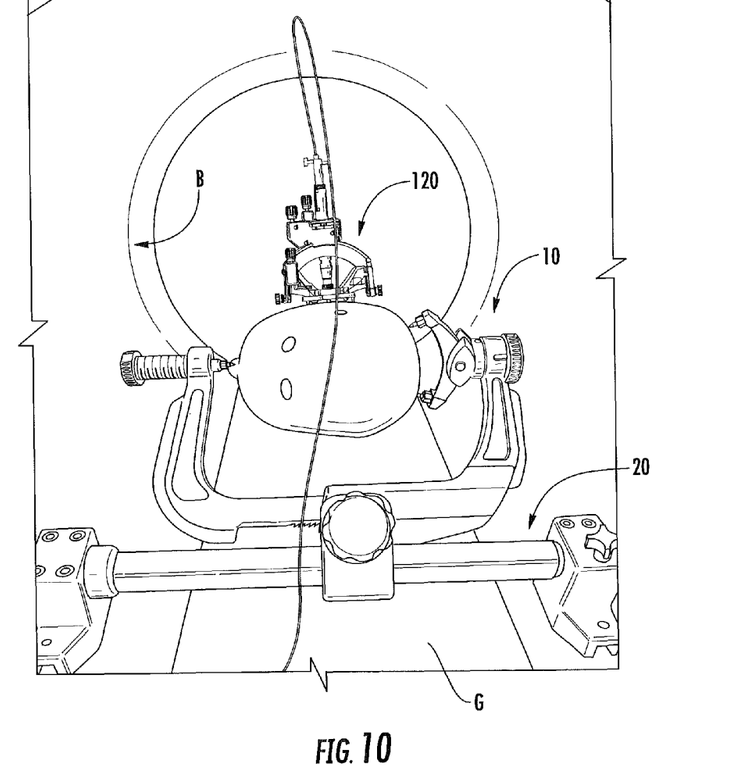
FIG. 10 illustrates the head fixation assembly of FIG. 8 with the targeting frame and the phantom patient head in a second orientation relative to the bore of the MRI magnet.

FIG. 9 illustrates the head fixation assembly 10 with the targeting frame 120 and patient head H in a first orientation relative to the bore B of the MRI magnet. FIG. 10 illustrates the head fixation assembly 10 with the targeting frame 120 and patient head H in a second orientation relative to the bore B of the MRI magnet.

FIG. 11 illustrates a pair of flexible, commercial MRI coils 130 that can cooperate with the head fixation assembly 10, according to some embodiments of the present invention. The coils 130 can reside inside the pins 89, 96 about a respective patient's head.

All of the components of the head fixation assembly 10 described above (i.e., the base 20, the head support frame 60, etc.) are formed from or include MRI-compatible material. Exemplary MRI-compatible (non-ferromagnetic) materials include, but are not limited to, various polymeric materials (e.g., plastics), carbon fiber materials, glass-filled epoxies, and metals such as nickel-titanium alloys (e.g., Nitinol). As known to those skilled in the art of MRI, Nitinol is non-ferromagnetic with a lower magnetic susceptibility than conventional stainless steel.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. An apparatus, comprising:
  a head support frame for immobilizing the head of a patient during a medical procedure within a bore of an MRI scanner, wherein the head support frame comprises a shaft extending outwardly therefrom, the shaft comprising a threaded portion;
  an elongated base configured to be secured to a gantry associated with the MRI scanner and to extend across a width of the gantry, wherein the base comprises first and second support members and an elongated member extending therebetween and movably coupled to the first and second support members such that the elongated member can rotate about its axis;
  a connector housing slidably secured to the elongated member, the connector housing comprising a bore configured to receive the shaft extending outwardly from the head support frame; and
  a locking member threadingly engaged with the threaded portion of the head support frame shaft, wherein tightening of the locking member secures the head support frame to the connector housing, prevents movement of the connector housing along the elongated member, and prevents rotation of the head support frame about the shaft, and wherein loosening of the locking member allows the head support frame to be rotated about the shaft and allows the connector housing and head support frame to be moved along the elongated member and positioned at any of a plurality of locations between the first and second support members.

2. The apparatus of claim 1, wherein one end of the elongated member comprises a first connector releasably engaged with a second connector secured to one of the support members, wherein the elongated member can rotate about its axis when the first and second connectors are disengaged from each other.

3. The apparatus of claim 1, wherein the base allows the head support frame to rotate about two orthogonal axes so as to be positioned at any of a plurality of angles relative to the gantry.

4. The apparatus of claim 1, wherein the elongated member has a substantially rectangular cross section.

5. The apparatus of claim 1, wherein the elongated member comprises a plurality of substantially flat, elongated surfaces with rounded edges between adjacent ones of the flat, elongated surfaces.

6. The apparatus of claim 1, wherein each support member comprises a lower surface that is oriented at an angle relative to a longitudinal direction of the elongated member.

7. The apparatus of claim 1, wherein each support member comprises a lower surface and a gripping element that extends outwardly from the lower surface.

8. The apparatus of claim 7, wherein gripping element extends outwardly from the lower surface at an angle relative to the lower surface.

9. The apparatus of claim 1, wherein the head support frame comprises a pair of head engagement arms extending outwardly from opposing sides of the base, wherein each head engagement arm comprises a free end,
wherein at least one head fixation member is associated with the free end of each respective arm, and wherein the head fixation members are configured to engage a patient's head within the head support frame.

10. The apparatus of claim 9, further comprises a flexible RF coil closely spaced to the free end of each head engagement arm of the head support assembly.

11. The apparatus of claim 1, wherein the elongated member has opposite first and second end portions, wherein each of the first and second end portions includes a free end portion that is received within a bore in a respective one of the first and second support members.

12. The apparatus of claim 11, further comprising a first connector that surrounds a free end portion of the elongated member, wherein the first connector that has a plurality of engagement teeth, and wherein a support that receives the free end portion includes a second connector that has a plurality of engagement teeth configured to mateably engage with the engagement teeth of the first connector to prevent axial rotation of the elongated member.

* * * * *

UNITED STATES PATENT AND TRADEMARK OFFICE
CERTIFICATE OF CORRECTION

| | | |
|---|---|---|
| PATENT NO. | : 9,031,636 B2 | Page 1 of 1 |
| APPLICATION NO. | : 13/781117 | |
| DATED | : May 12, 2015 | |
| INVENTOR(S) | : Peter Piferi | |

It is certified that error appears in the above-identified patent and that said Letters Patent is hereby corrected as shown below:

In the Claims:

Column 12, Claim 8, Line 4: Please correct "wherein gripping"
to read -- wherein the gripping --

Column 12, Claim 10, Line 15: Please correct "further comprises a"
to read -- further comprising a --

Column 12, Claim 12, Line 25: Please correct "connector that has"
to read -- connector has --

Signed and Sealed this
Twenty-sixth Day of January, 2016

Michelle K. Lee
*Director of the United States Patent and Trademark Office*